United States Patent
Chihani et al.

(10) Patent No.: US 6,194,630 B1
(45) Date of Patent: *Feb. 27, 2001

(54) SUPERABSORBENT FIBRE OR NONWOVEN MATERIAL, A METHOD FOR ITS MANUFACTURE, AND AN ABSORBENT ARTICLE COMPRISING THE SUPERABSORBENT FIBRE OR NONWOVEN MATERIAL

(75) Inventors: Thami Chihani, Mölnlycke; Göran Canbäck, Västra Frölunda; Urban Wecke; Thomas Hjertberg, both of Göteborg, all of (SE)

(73) Assignee: SCA Hygiene Products Aktiebolag, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/617,797
(22) PCT Filed: Aug. 30, 1994
(86) PCT No.: PCT/SE94/00797
  § 371 Date: Mar. 7, 1996
  § 102(e) Date: Mar. 7, 1996
(87) PCT Pub. No.: WO95/08353
  PCT Pub. Date: Mar. 30, 1995

(30) Foreign Application Priority Data

Sep. 22, 1993 (SE) .................................................. 9303092

(51) Int. Cl.[7] .......................... A61F 13/15; B32B 31/20; B32B 27/02; D02G 3/00
(52) U.S. Cl. ........................ 604/366; 604/368; 604/370; 156/308.2; 156/309.9; 428/372; 442/170; 442/171; 442/417
(58) Field of Search .................................. 604/365, 366, 604/368, 370, 372, 378; 156/308.2, 309.9, 271; 428/283, 286, 296, 372; 442/170, 171, 417

(56) References Cited

U.S. PATENT DOCUMENTS

| 3,998,988 | 12/1976 | Shimomai et al. . |
| 4,128,692 | 12/1978 | Reid . |

(List continued on next page.)

FOREIGN PATENT DOCUMENTS

| 2 164 262 | 8/1972 | (DE) . |
| 29 40 183 | 4/1980 | (DE) . |
| 0080382 | 6/1983 | (EP) . |
| 0 202 472 | 11/1986 | (EP) . |
| 0273141 | 7/1988 | (EP) . |
| 0402650 | 12/1990 | (EP) . |
| 0612533 | 8/1994 | (EP) . |
| 2194255 | 3/1988 | (GB) . |
| 2203985 | 11/1988 | (GB) . |
| 90/11181 | 10/1990 | (WO) . |
| 91/10413 | 7/1991 | (WO) . |

OTHER PUBLICATIONS

Bruno Vollmert "Grundriss der Makromolekularen Chemie", 1988, Band IV, pp. 198–200.

Primary Examiner—John G. Weiss
Assistant Examiner—K. M. Reichle
(74) Attorney, Agent, or Firm—Burns, Doane, Swecker & Mathis, L.L.P.

(57) ABSTRACT

A superabsorbent fiber or a nonwoven material including a thermoplastic polymeric fiber to which solid particles of superabsorbent material have been thermobonded by heating the polymeric fiber to a temperature at which adhesion is obtained between the fiber and the particles and a method of making the same. Also, an absorbent article is produced including such a superabsorbent fiber or nonwoven material.

21 Claims, 3 Drawing Sheets

U.S. PATENT DOCUMENTS

| | | |
|---|---|---|
| 4,160,059 | 7/1979 | Samejima . |
| 4,297,410 | 10/1981 | Tsuchiya et al. . |
| 4,354,487 | 10/1982 | Oczkowski et al. . |
| 4,449,977 | 5/1984 | Korpman . |
| 4,590,114 * | 5/1986 | Holtman ................................ 604/370 |
| 4,721,647 | 1/1988 | Nakanishi et al. . |
| 4,797,318 | 1/1989 | Brooker et al. . |
| 4,888,238 | 12/1989 | Katz et al. . |
| 5,002,814 | 3/1991 | Knack et al. . |
| 5,149,334 * | 9/1992 | Lahrman et al. .................... 607/368 |
| 5,188,624 | 2/1993 | Young, Sr. et al. . |
| 5,231,122 * | 7/1993 | Palumbo et al. ..................... 604/370 |
| 5,368,918 * | 11/1994 | Harada et al. ....................... 604/366 |
| 5,531,728 * | 7/1996 | Lash ..................................... 604/366 |

* cited by examiner

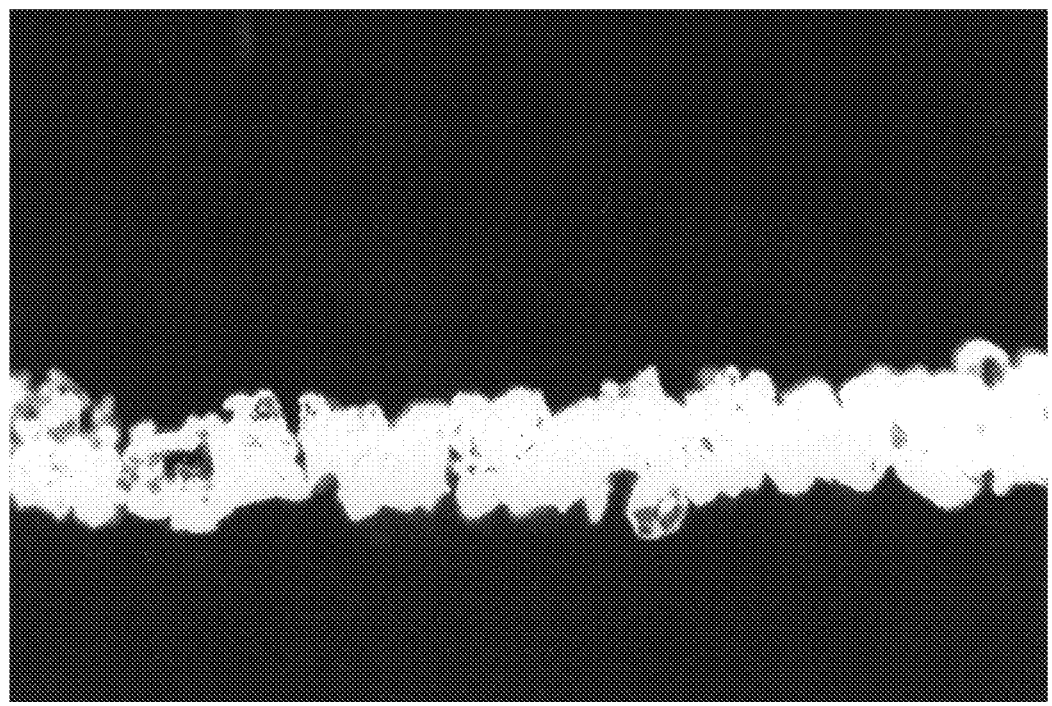
FIG. 1
FIG. 2
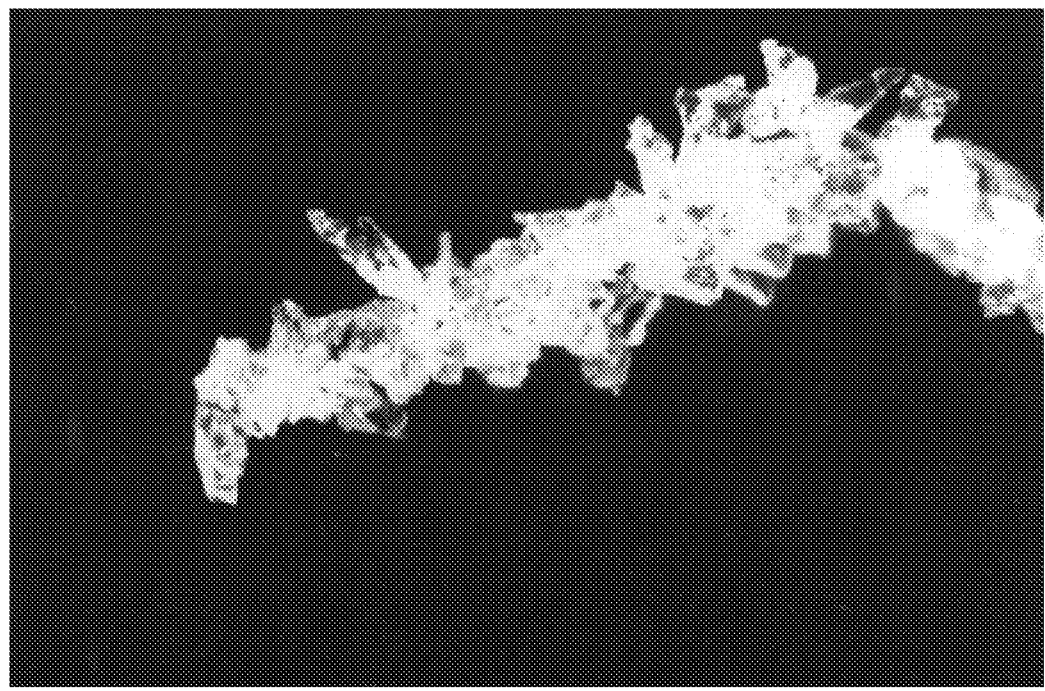

SUPERABSORBENT FIBRE OR NONWOVEN MATERIAL, A METHOD FOR ITS MANUFACTURE, AND AN ABSORBENT ARTICLE COMPRISING THE SUPERABSORBENT FIBRE OR NONWOVEN MATERIAL

TECHNICAL FIELD

The present invention relates to superabsorbent fibres or non-woven materials in which particles of superabsorbent material have been bonded to individual fibres. The invention also relates to a method of producing the superabsorbent fibres or nonwoven material concerned, and to absorbent articles that contain the same.

BACKGROUND ART

It is known to admix particles of water-insoluble hydrogels, so-called superabsorbents, in fibre structures for absorption purposes, for instance absorbent bodies in diapers, sanitary napkins, incontinence guards, wound dressings etc. These superabsorbents are polymeric materials that are capable of absorbing large quantities of liquid. One problem encountered when mixing superabsorbents in fibre structures is to fix the superabsorbent particles in the structure so as to localize the superabsorbent in the correct position in the product, and so that the product can be handled in manufacture and during transportation without the superabsorbent being redistributed in the product or shaken from the fibre structure. Dusting caused by fine-grain superabsorbents can also lead to an environmental problem at the place of manufacture.

Several methods of adhering superabsorbent to fibres are known to the art. According to one method described in U.S. Pat. No. 4,354,487 and EP-A-0,402,650, a monomeric solution is allowed to infiltrate a fibre network or is mixed with free fibres. The monomers are then allowed to polymerize in place on the fibres. Prior publication U.S. Pat. No. 4,888,238 describes a method in which dissolved polyelectrolytes form complex bonds on the fibres. According to another method, described in U.S. Pat. No. 4,128,692, fibres are first suspended in water and the superabsorbent is then added and precipitates onto the fibres. In all of the aforesaid cases it is necessary to evaporate-off the solvent, i.e. the water, in one way or another, after having bound the superabsorbent to the fibres. This is difficult to achieve when the water is bonded firmly to the superabsorbent.

According to another method, described in U.S. Pat. No. 4,721,647, a water-soluble monomer having double bonds is allowed to form droplets around a hydrophobic fibre, these droplets being allowed to polymerize and form cross-links. The underlying concept is that the superabsorbent shall embrace the fibre so as not to be released when absorbing liquid. According to the measurements reported in said patent, less than 20% by weight of the superabsorbents are released in the process of absorption. It is also mentioned in the patent that the absorbent droplets should not be applied too densely, since this would stiffen the fibres.

Another method of adhering superabsorbents to fibres is described in WO 90/11181 and WO 91/10413, according to which fibres are coated with a binder which binds to superabsorbent particles. The binder may consist of an ethylene vinyl acetate copolymer, ethylene acrylic acid copolymer, polyvinyl chloride or some other thermosetting resin, for instance. The binder is sprayed onto the fibres a number of times, so as to effectively cover the fibre surfaces. Absorbent grains are then applied to the fibres before the binder has set. Between 15 and 50 % by weight of the absorbents, based on the dry fibre weight, are bonded when practicing this method, which is about equal to the amount of superabsorbents that is effectively bonded when practicing the other methods aforesaid.

U.S. Pat. No. 5,002,814 discloses another solution to the problem, in which a particle of a superabsorbent polymer has been bound to several short fibres.

SUMMARY OF THE INVENTION

The object of the present invention is to bind superabsorbent particles directly to essentially all surfaces of individual fibres so that distribution of the superabsorbents in a fibre structure can be better controlled. Adhesion between superabsorbent and fibre should preferably be relatively low or weak, so as not to limit to any great extent the swelling space that is available to the superabsorbents when absorbing liquid. Binding of the superabsorbent particles to the fibres shall also be effected without the aid of a solvent that must later be evaporated off, and also while avoiding the application of binder to the fibre.

This object has been achieved in accordance with the invention in that the individual fibre or at least a part of the individual fibres present in the nonwoven material is comprised of a thermoplastic polymer fibre to which solid particles of superabsorbent material have been directly thermobonded by heating said fibre to a temperature at which adhesion between fibre and particles is achieved.

Synthetic fibres may be fully crystalline, i.e. contain 100% crystalline material, although they may alternatively contain varying percentages of crystalline material. A high degree of stretching in connection with manufacturing the fibre will produce a high proportion of crystalline material. Partially crystalline fibres (0–40%) are preferably used in accordance with the invention, such fibres providing good adhesion at low temperatures. One speaks about the softening temperature or glass transition temperature ($T_g$) in the case of amorphous fibres.

In the case of fibres that are part crystalline and part amorphous, the amorphous material will be soft at temperatures between the softening temperature and the crystalline melting point, whereas the crystalline material will still be hard. There is thus obtained a certain degree of adhesion, which improves, however, when the crystalline melting point is exceeded.

When the thermoplastic fibre consists of a crystalline or partly crystalline fibre, the crystalline melting point of the fibre will suitably not be higher than 300° C., and preferably not higher than 270° C. When the thermoplastic fibre is an amorphous fibre, its softening or glass transition temperature will preferably not be higher than 100° C.

The fibre may be comprised, for instance, of a polyolefin, such as polyethylene or polypropylene, polyester, polyamide, bicomponent fibre, or a copolymer of ethylene and acrylic/methacrylic acid or ethylene and vinyl acetate.

The superabsorbent particles will suitably have a mean particle size of up to 500 μm.

The invention also relates to a method of producing the superabsorbent fibre or nonwoven material concerned, this method being characterized by bringing solid particles of superabsorbent material directly into contact with essentially all surfaces of an individual thermoplastic polymeric fibre or a nonwoven material which includes thermoplastic polymeric fibres, said fibre being heated or having been heated to a temperature at which the superabsorbent particle adheres directly to the individual fibre, and thereafter allowing the mixture to cool.

The invention also relates to an absorbent article, such as a diaper, sanitary napkin, incontinence guard and the like, which is characterized in that the article has at least one absorbent layer which includes superabsorbent fibres or nonwoven material according to the invention, optionally in combination with other fibres, such as cellulose fibres.

BRIEF DESCRIPTION OF THE DRAWINGS

The invention will now be described in more detail with reference to exemplifying embodiments thereof and also with reference to the accompanying drawings, in which FIGS. 1 and 2 are enlarged photocopies of photographs illustrating a fibre to which superabsorbent particles of different size fractions have been bonded;

FIGS. 8 and 9 are schematic longitudinal section views of an absorbent body included in an absorbent article, such as a diaper, sanitary napkin, incontinence guard or the like.

DESCRIPTION OF EXEMPLIFYING EMBODIMENTS

Figure 3:
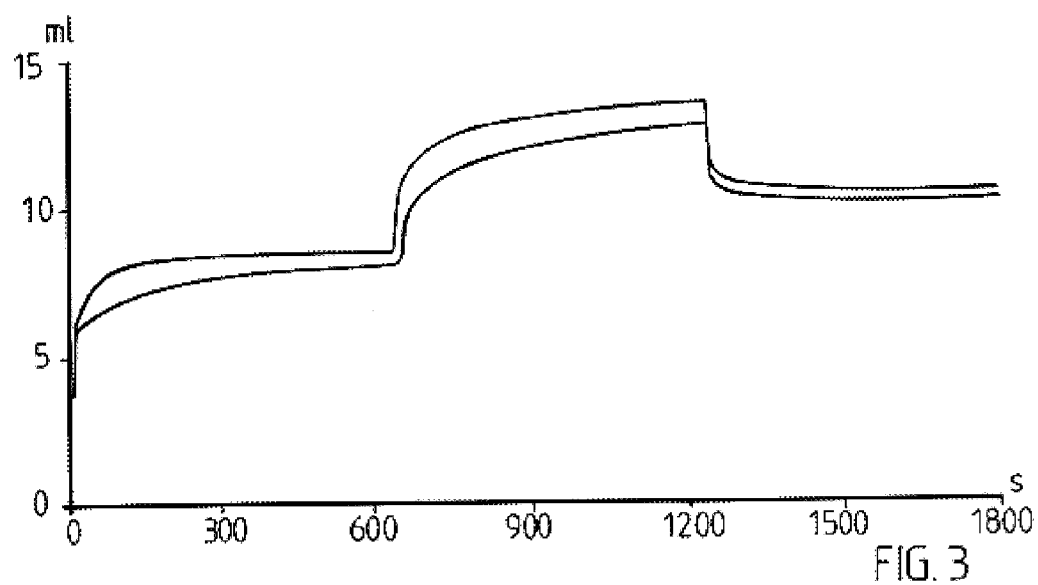
FIG. 3 is an absorption curve from a demand wetting test.

Synthetic fibres comprised of two different polymers have been used in the following tests, the one being an ethylene acrylic acid copolymer, EAA, containing 5.7 mol-% acrylic acid, and the other being an ethylene vinyl acetate copolymer, EVA, containing 3.1 mol-% vinyl acetate. The crystalline melting point of the EAA-polymer was about 94° C., and in the case of the EVA-polymer about 97° C. The fibres each had a length of about 1 cm and the EAA-fibre had a thickness of 21 dtex and the EVA-fibre had a thickness of 11 dtex. The superabsorbent polymer used was Nippon-Shokubais AQUALIC CA W3, which is a sodium salt of open structure cross-linked polyacrylic acid.

The superabsorbent was ground so as to increase the quantity of suitably sized particles that fasten to the fibres and in order to investigate the possible influence on the absorption properties. The ground superabsorbent was screened to obtain a desired size distribution.

With the intention of adhering superabsorbent particles directly to essentially all surfaces of the individual polymer fibre, a mixture of fibres and superabsorbent particles was heated to a given temperature over a given period of time, more specifically to a temperature of 140° C. over a time period of 10 min.

A series of tests was carried out on different fractions of superabsorbent particles with the intention of studying the appearance of the fibres and to determine the quantities in which the absorbent had bonded to the fibres. Fractions of sizes 300–500 μm, 150–300 μm, 90–150 μm and 38–90 μm were investigated. The tested fibre was an EAA-fibre.

In the case of the smallest superabsorbent fraction, 38–90 μm, the amount of superabsorbent that bonded to the fibre corresponded to 0.38 times the weight of the fibre. This factor is calculated in accordance with the following:

$$K_{SF} = \frac{m_{SF} - m_f}{m_f}$$

where $K_{SF}$=index for the amount of bonded super-absorbent $M_f$=weight of fibre without superabsorbent $m_{SF}$=weight of fibre with bonded superabsorbent.

In the case of the next fraction, 90–150 μm, the amount of superabsorbent that bonded to the fibre corresponded to 2.46 times the weight of the fibre. In the case of the fractions 150–300 μm, the amount of bonded superabsorbent corresponded to 6.4 times the fibre weight, while in the case of the largest fraction, 300–500 μm, the amount of superabsorbent that bonded to the fibre corresponded to 16.6 times the fibre weight. FIGS. 1 and 2 are enlarged photographic views of an EAA-fibre with bonded superabsorbent particles of the size fraction 90–150 μm and 150–300 μm respectively.

By way of comparison, unscreened and unground superabsorbent has been bonded to an EAA-fibre, the amount of superabsorbent binding to the fibre corresponding to 13.3 times the weight of said fibre.

EVA-fibres were also coated with a superabsorbent from the size fraction 90–150 μm at the same temperature, 140° C. for 10 min, resulting in roughly the same amount of bound superabsorbent as in the case of the EAA-fibre, i.e. 2.17 times the fibre weight.

Tests were also carried out in which the fibre was coated with superabsorbents of the same size fraction but while applying other temperatures. The fraction used was the 90–150 μm fraction and the fibres were EAA-fibres. When heating to a temperature of 110° C., the amount of superabsorbent that bonded to the fibres corresponded only to 0.26 times the fibre weight, despite extending the treatment time to 30 minutes. Only a small part of the fibre surface area was coated with superabsorbent. When heating to a higher temperature, 170° C. for 10 min, the amount of bonded superabsorbent was 2.7 times the fibre weight.

At higher temperatures, and noticeably at 170° C., the superabsorbent particles not only bond to the fibre, but also to one another and form large agglomerates. This problem is greatly reduced when using unground superabsorbent, which is probably because the superabsorbent particles exhibit a hydrophobic surface modification which disappears when grinding the superabsorbent.

Thus, the amount of superabsorbent that binds to the fibres depends on heating temperature and particle size. The temperature would appear to be of little significance after having reached a sufficiently high temperature for the whole of the fibre surface to start binding superabsorbent. This occurs when the crystalline melting point of the fibre has been exceeded.

When admixing fibres with the adhesive superabsorbent particles in a cellulose fibre structure, no free particles that had fallen through the structure could be observed. Whether or not sufficient adhesion has been achieved can also be determined by extending the fibre to twice its length for instance and checking whether or not all superabsorbent particles are still bonded to the fibre.

Absorption Measurements

1. The Tea Bag Method

Dip absorption for the two components and for the finished fibre with superabsorbent particles bound thereon was measured by the tea bag method. According to this method, the sample is placed in a bag measuring about 5×5 cm and the bag is then sealed around its perimeter. The bag is then placed in a dish with an excess of 0.9% sodium chloride solution and the sample is allowed to swell freely in the bag. The amount of sample present should not cause absorption to be restricted by the size of the bag. The sample is removed from the salt solution at given time points and allowed to drain for one minute and is then weighed. Upon completion of the measuring process in total, the bag is centrifuged at 1.5 g for 10 min, whereafter the bag is weighed to provide a retention value, i.e. a value of the ability of the sample to retain the absorbed liquid under pressure.

Absorption can be calculated from the weight of the bags in accordance with the following formula:

$$A_s = \frac{m_m - m_b(1 + A_b) - ms}{m_s}$$

where $A_S$=sample absorbency
$A_b$=tea bag material absorbency
$m_m$=weight of tea bag with sample after absorption
$m_b$=weight of empty, dry tea bag
$m_s$=weight of dry sample.

The retention has been calculated as the absorbency after centrifugation, divided by absorbency prior to centrifugation. The calculation has been made on the mean value of four bags in a sample series.

When measuring free fibres, a sample weight of about 0.1 g per bag was used, which is slightly more than one fifth of the weight of the bag. A sample weight of about 0.2 g per bag was used for the superabsorbent. Measurements on fibres having bonded superabsorbent particles were made with a sample size based on the amount of bonded superabsorbent. This sample size was about 0.1 g per bag. The size fraction used was 90–150 µm. The results of these measurements are reported in Table 1 below.

TABLE 1

| Sample | Abs after 1 min g/g | Abs. after 5 min g/g | Abs. after 30 min g/g | Abs. after 60 min. g/g | Retention % |
|---|---|---|---|---|---|
| EAA-fibre | 18.8 | 15.8 | 16.7 | 17.8 | 0 |
| EVA-fibre | 17.4 | 17.6 | 16.2 | 16.0 | 0 |
| Screened unground superabsorbent | 39.9 | 42.1 | 41.6 | 41.4 | 56 |
| Screened ground superabsorbent | 50.3 | 53.2 | 52.3 | 52.1 | 68 |
| Screened ground superabsorbent heated to 140° C. for 10 min. | 51.4 | 52.6 | 52.0 | 52.0 | 68 |
| Screened ground superabsorbent heated to 170° C. for 10 min | 51.0 | 51.5 | 50.9 | 51.0 | 69 |
| EAA-fibre with bonded superabs. produced at 140° C. for 10 min. | 40.0 | 40.1 | 39.8 | 39.4 | 62 |
| EAA-fibre with bonded superabs. produced at 170° C. for 10 min. | 39.8 | 40.7 | 40.2 | 40.0 | 62 |
| EVA-fibre with bonded superabs. produced at 140° C. for 10 min. | 40.7 | 39.5 | 38.8 | 38.9 | 60 |

In order to evaluate the absorption of the prepared fibres with superabsorbent particles fastened thereon, a comparison absorbency value has been calculated from the absorption of the fibres and absorbent. This value has been calculated in accordance with the following:

$$A_t = V_f A_f + V_{SAP} A_{SAP}$$

where $A_t$=the theoretical comparison absorbency value
$A_f$=the absorbency of the fibre
$A_{SAP}$=the absorbency of superabsorbent particles of the same size fraction and the same thermal history
$V_f$=the fibre weight fraction
$V_{SAP}$=superabsorbent weight fraction This calculated value was then compared with the absorption value $A_S$, which was calculated from the weight of the total sample as beforementioned. This comparison is included in Table 2 below.

TABLE 2

Experimental and theoretical absorption values

| | | | 1 min g/g | 5 min g/g | 30 min g/g | 60 min g/g | Retention % |
|---|---|---|---|---|---|---|---|
| EVA 140° C. | $V_{SAP}$ = 0.6826 $V_f$ = 0.3174 | $A_s$ $A_t$ | 40.7 41 | 39.5 41 | 38.8 41 | 38.9 41 | 60 59 |
| EAA 140° C. | $V_{SAP}$ = 0.7100 $V_f$ = 0.2900 | $A_s$ $A_t$ | 40.0 42 | 40.1 42 | 39.8 42 | 39.4 42 | 62 60 |
| EAA 170° C. | $V_{SAP}$ = 0.7344 $V_f$ = 0.2656 | $A_s$ $A_t$ | 39.8 42 | 40.7 42 | 40.2 42 | 40.0 42 | 62 62 |

2. Demand Wetting

Absorbency under load was measured with the aid of a so-called demand wetting method. The sample is subjected to load from above and the liquid allowed to penetrate up in the sample through a glass filter on which the sample rests. The upper surface of the glass filter is positioned on a higher level than the surface of the reservoir, with which the liquid communicates, so as to obtain a negative hydrostatic pressure. The liquid used was a 0.9% by weight sodium chloride solution and the negative pressure was 0.2 kPa. The sample load was applied cyclically at 10 min intervals. The load was 7.5 kPa during the first interval, 0.57 kPa during the second interval and again 7.5 kPa during the last interval. The sample body was a 5 mm thick plate having a diameter of 50 mm and comprised of air-laid cellulose fluff.

Absorption under load was measured on sample bodies in the form of a fibre network. Measurements were made on four mutually different samples: pure cellulose, cellulose air-mixed with superabsorbent particles of size fraction 90–150 µm, cellulose air-mixed with fibres having bonded thereto superabsorbent particles of the same size fraction as the free particles and cellulose with a layer of the same fibres as those above. The cellulose fibres were CTMP-fluff and the fibre used was EAA-fibre produced at 140° C. over a period of 10 min.

FIG. 3 shows the amount of salt solution absorbed as a function of time in respect of two different samples, one consisting of cellulose fibres air-mixed with free superabsorbent particles, and one consisting of cellulose fibres air-mixed with fibre-bonded superabsorbent. The upper curve applies to cellulose having free superabsorbent particles, while the bottom curve applies to cellulose having fibre-bonded superabsorbent particles. The load on the sample was lowered from 7.5 kPa to 0.57 kPa after 10 min and was raised again to 7.5 kPa after 20 min. The curve representing fibres having fibre-bonded superabsorbent particles in a fluff layer was about 1.5 ml beneath the curve representing the sample with air-mixed fibre. These values are not shown in FIG. 3.

Study of the Absorption Process

Figure 4:
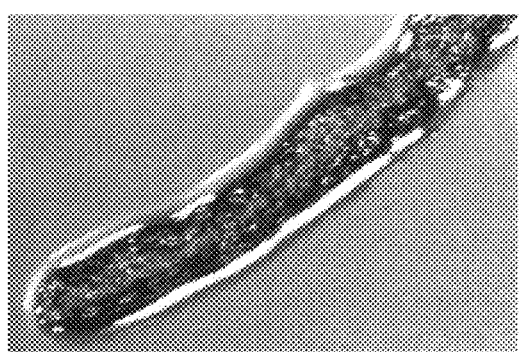
FIGS. 4–7 are photocopies of photographs of an inventive fibre during different stages of an absorption process.
Figure 5:
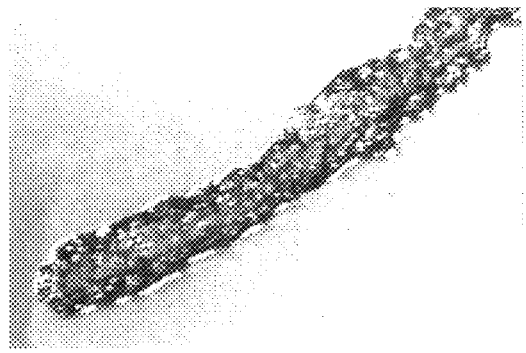
Figure 6:
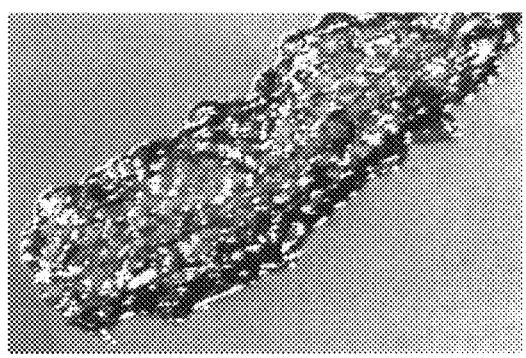
Figure 7:
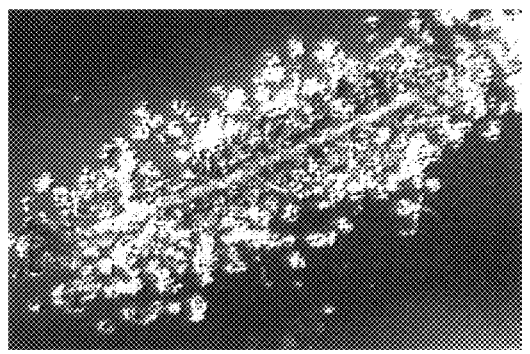

The course followed by the actual absorption process has been studied by allowing a fibre to absorb water droplets from one end while recording the process on a video film with the aid of a microscope. The droplets wet the superabsorbent and spread over the length of the fibre, see FIG. 4, whereafter a gel is formed, FIG. 5. FIG. 6 shows the fibre after a much larger amount of solution has been absorbed. When the fibre is allowed to dry in air, the superabsorbent particles will dry and release their bond with the fibre, as shown in FIG. 7.

All photographs, FIGS. 4–7, show an EAA-fibre with bonded superabsorbent particles of size fraction 90–150 $\mu$m produced at 140° C. for 10 min. EVA-fibres have also been studied in the same way and with the same results.

The bond between superabsorbent particles and fibres is a weak or relatively low bond having a predetermined weakness broken. The bond is weak enough to be in the process of absorption. This means that the absorbancy of the superabsorbents when swelling freely is not influenced by being bonded to a fibre, which is also shown by the aforesaid absorption calculated from the absorption of the superabsorbent and the fibre. Absorption measurements taken with the aid of the demand wetting method show that samples which included fibre-bonded superabsorbent particles absorbed liquid at a slightly slower rate than samples that contained free particles. This is probably because the fibres containing superabsorbents enlarge the pores of the fibre network, causing slower absorption in the sample.

In order for the superabsorbent particles to loosen as liquid is absorbed, the use of permanent bonds shall be avoided so that as the superabsorbents swell the liquid or the force thus generated will cause the superabsorbent particles to loosen from the fibre. In that way gel blocking is prevented. Examples of appropriate weak or relatively low bonds are different types of physical (van der Waal's -forces) and ionic bonds.

The physical bonds shall be capable of providing good adhesion between fibre and superabsorbent particles. In the examples described above, acid-based interaction has been utilized, together with the possibility of dimer formation between acrylic acid groups. Diffusion of molecular chains over the boundary surface or interface between fibre and superabsorbent also contributes towards adhesion, although it should be limited so as not to prevent the superabsorbent particles from loosening after absorption.

The fibre polymer shall wet the superabsorbent particles so as to achieve good contact. The contact angle $\theta$ between the polymer melt and the superabsorbent particle will preferably be lower than 90°.

In those tests reported in the aforegoing, fibres of the copolymers EAA and EVA have been used. It will be understood, however, that other thermoplastic fibres can be used, such as polyolefins, e.g. polyethylene, polypropylene etc. Bicomponent fibres having a core, e.g. of polyester or polypropylene and a casing, e.g. of polyethylene, which has a lower crystalline melting point than the core material, are also useful.

The invention can also be applied on nonwoven material in which at least some of the fibres included are comprised of thermoplastic polymer fibre of the aforesaid kind. The superabsorbent particles are fastened to the fibres in the nonwoven material in a manner corresponding to that used in the case of loose fibres, i.e. the nonwoven material is heated to a temperature at which the superabsorbent particles will adhere to the thermoplastic fibres in the material. The thermoplastic fibres are preferably comprised of bicomponent fibres, although other thermoplastic fibres can also be used.

The term superabsorbent particles shall be given a relatively wide interpretation in the present context and shall be considered to include superabsorbent grains, granules, flakes and short fibres. The chemical composition of the superabsorbent may also be varied, and any particulate superabsorbent that has been found to possess absorption properties suitable for the present purpose may be used. Mixtures of different superabsorbents may, of course, be used.

Figure 8:
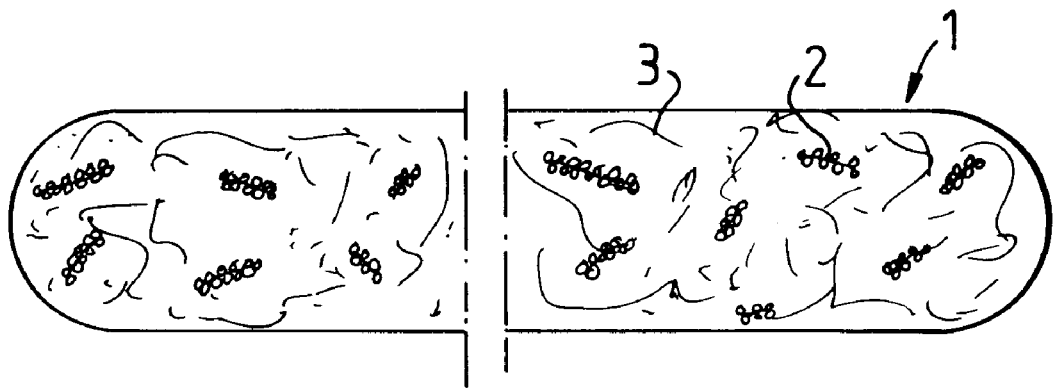
Figure 9:
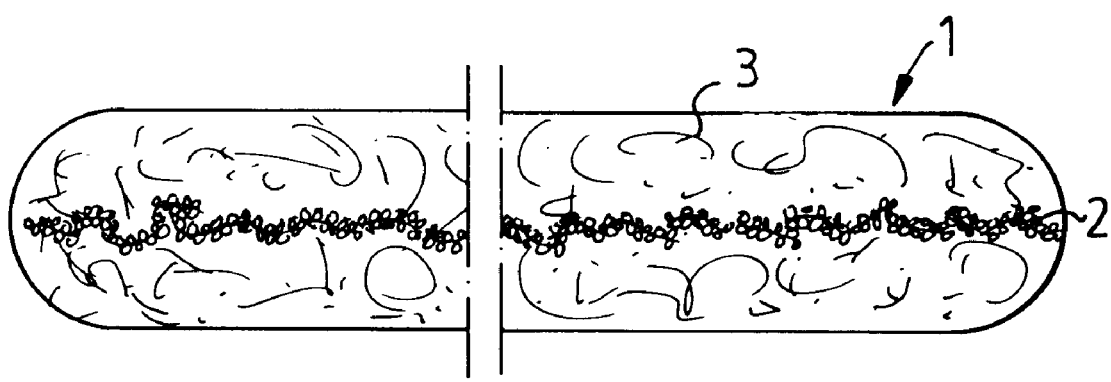

FIGS. 8 and 9 illustrate schematically two exemplifying embodiments of absorbent bodies 1 or the layers of absorbent bodies intended for such absorbent articles as diapers, sanitary napkins, incontinence guards and the like. In the example shown in FIG. 8, superabsorbent fibres 2 according to the invention are mixed with other fibres 3, for instance cellulose fibres. The superabsorbent fibres 2 and the cellulose fibres 3 can be mixed and shaped to an absorbent body, for instance by a conventional air laying process. In the example illustrated in FIG. 9, the superabsorbent fibres 2 are applied in the form of a layer between a surrounding layer of other fibres 3, for instance cellulose fibres. In this case, it is conceivable that the fibres 2 are bound to one another and form a nonwoven material. The surrounding fibre layers 3 may alternatively consist of tissue layers.

Localization of the superabsorbent fibres 2 in the absorbent body may be varied so that some parts of the absorbent body will contain a greater percentage of superabsorbent fibres than other parts of the body. The inventive superabsorbent fibres 2 may also be combined with other superabsorbents.

What is claimed is:

1. A superabsorbent fibre, comprising:
   an individual thermoplastic polymeric fibre;
   solid particles of superabsorbent material thermobonded directly to and coating essentially all surfaces of the individual polymeric fibre by heating the polymeric fibre to a temperature at which adhesion is achieved between said fibre and solid particles;
   wherein the thermobond is a weak bond having a predetermined weakness and the thermobond is formed between the individual polymeric fibre and the solid particles, said predetermined weakness being defined such that the thermobond is broken during absorption; and
   wherein the particles have a particle size of 90–300 $\mu$m.

2. A fibre according to claim 1, wherein the thermoplastic polymeric fibre is at least partially comprised of a crystalline material and has a crystalline melting point not higher than 300° C.

3. A fibre according to claim 2, wherein the thermoplastic polymeric fibre is a polyolefin.

4. A fibre according to claim 2, wherein the thermoplastic polymeric fibre is a bicomponent fibre.

5. A fibre according to claim 2, wherein the thermoplastic polymeric fibre is a copolymer of ethylene and acrylic acid or methacrylic acid, or a copolymer of ethylene and vinyl acetate.

6. A fibre according to claim 2, wherein the thermoplastic polymeric fibre has a crystalline melting point not higher than 270° C.

7. A fibre according to claim 3, wherein the polyolefin is polyethylene.

8. A fibre according to claim 3, wherein the polyolefin is polypropylene.

9. A fibre according to claim 3, wherein the polyolefin is polyester.

10. A fibre according to claim 3, wherein the polyolefin is polyamide.

11. A fibre according to claim 1, wherein the thermoplastic fibre consists of an amorphous material having a softening temperature not higher than 100° C.

12. A fibre according to claim 1, wherein the particles have a particle size of 90–150 μm.

13. A method of producing the superabsorbent fibre according to claim 1, said method comprising the steps of:
  bringing solid particles of superabsorbent material into contact with all surfaces of the individual thermoplastic polymeric fibre,
  heating the individual fibre to a temperature at which the superabsorbent particles will adhere to the individual fibre, and permitting the particle covered individual fibre to cool.

14. A method according to claim 13, wherein said heating step includes heating the fibre to a temperature which exceeds the crystalline melting point of the fibre in case the thermoplastic fibre is at least partially comprised of a crystalline material.

15. A method according to claim 13, wherein said heating step includes heating the fibre to a temperature above its softening temperature in case the thermoplastic fibre is comprised of an amorphous material.

16. An absorbent article, wherein said absorbent article includes at least one absorption layer comprising a plurality of superabsorbent fibres according to claim 1.

17. An absorbent article according to claim 16, wherein the superabsorbent fibres are mixed with other fibres.

18. An absorbent article according to claim 16, wherein the superabsorbent fibres are applied in a layer between layers of other fibres.

19. A method of producing a nonwoven material including said superabsorbent fibre according to claim 1, said method comprising the steps of:
  bringing said solid particles of superabsorbent material into direct contact with nonwoven material that contains a plurality of said individual thermoplastic fibres,
  heating said fibres to a temperature at which the superabsorbent particles will adhere to the individual fibres, and permitting the mixture to cool.

20. A fibre according to claim 1, wherein the particles have a particle size of 150–300 μm.

21. A nonwoven material, comprising:
  a plurality of individual thermoplastic polymeric fibres;
  solid particles of superabsorbent material thermobonded directly to the plurality of individual thermoplastic polymeric fibres and coating essentially all surfaces of each of the individual polymeric fibres by heating the polymeric fibres to a temperature at which adhesion is achieved between said fibres and solid particles;
  wherein the thermobond is a weak bond having a predetermined weakness and the thermobond is formed between the individual polymeric fibre and the solid particles, said predetermined weakness being defined such that the thermobond is broken during absorption; and
  wherein the particles have a particle size of 90–300 μm.

* * * * *